US008718973B2

(12) United States Patent
Ye et al.

(10) Patent No.: US 8,718,973 B2
(45) Date of Patent: May 6, 2014

(54) METHOD, DEVICE, AND SYSTEM FOR CALCULATING A GEOMETRIC SYSTEM MODEL USING AN AREA-SIMULATING-VOLUME ALGORITHM IN THREE DIMENSIONAL RECONSTRUCTION

(75) Inventors: Hongwei Ye, Kenosha, WI (US); Wenli Wang, Briarcliff Manor, NY (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 431 days.

(21) Appl. No.: 13/229,375

(22) Filed: Sep. 9, 2011

(65) Prior Publication Data

US 2013/0066589 A1 Mar. 14, 2013

(51) Int. Cl.
  *G06F 15/00* (2006.01)
  *G01T 1/20* (2006.01)
  *G01T 1/29* (2006.01)

(52) U.S. Cl.
  CPC .................................. *G01T 1/2985* (2013.01)
  USPC ..................................... 702/158; 250/363.04

(58) Field of Classification Search
  CPC ...................................................... G01T 1/2985
  USPC ....................................................... 702/158
  See application file for complete search history.

(56) References Cited

U.S. PATENT DOCUMENTS

| 6,762,794 B1 * | 7/2004 | Ogino | 348/262 |
| 2006/0262969 A1 * | 11/2006 | Matsumoto | 382/131 |
| 2010/0284600 A1 | 11/2010 | Yamada | |

FOREIGN PATENT DOCUMENTS

| JP | 11-511551 | 10/1999 |
| WO | WO 97/08569 | 3/1997 |
| WO | WO 2009/093305 A1 | 7/2009 |

OTHER PUBLICATIONS

Robert L. Siddon, "Fast calculation of the exact radiological path for a three-dimensional CT array", Medical Physics, vol. 12, No. 2, pp. 252-255, Mar./Apr. 1985.

Shih-Chung B. Lo, "Strip and Line Path Integrals with a Square Pixel Matrix: A Unified Theory for Computational CT Projections," IEEE Transactions on Medical Imaging, vol. 7, No. 4, pp. 355-363, Dec. 1988.

Ronald B. Schwinger, et al., "Area weighted convolutional interpolation for data reprojection in single photon emission computed tomography," Med. Phys., vol. 13, No. 3, pp. 350-353, May/Jun. 1986.

(Continued)

*Primary Examiner* — Bryan Bui
(74) *Attorney, Agent, or Firm* — Oblon, Spivak, McClelland, Maier & Neustadt, L.L.P.

(57) ABSTRACT

A method, device, and system for calculating first and second distance ratios used to calculate a geometric probability between a voxel and a tube-of-response (TOR). The method includes determining a first-edge-line including a first-middle-point, determining a second-edge-line including a second-middle-point, determining a middle line of the TOR, projecting a first point of a first surface of the voxel to the middle line, projecting a second point of a second surface of the voxel to the middle line, calculating a first distance between one of the first and second middle-points and the first-projected-point, and a second distance between the one of the first and second middle-points and the second-projected-point, and determining a first distance ratio based on the first and second distances. The method calculates the second distance ratio similarly to the first distance ratio. The geometric probability is proportional to the product of the first and second distance ratios.

15 Claims, 11 Drawing Sheets

(56) References Cited

OTHER PUBLICATIONS

J. Gregor, et al., "Approximate Volumetric System Models for MicroSPECT," IEEE Transactions on Nuclear Science, vol. 53, No. 5, pp. 2646-2652, Oct. 2006.

Jürgen J. Scheins, et al., "Analytical Calculation of Volumes-of-Intersection for Iterative, Fully 3-D PET Reconstruction," IEEE Transactions on Medical Imaging, vol. 25, No. 10, pp. 1363-1369, Oct. 2006.

Bruno De Man, et al., "Distance-driven projection and backprojection in three dimensions", Physics in Medicine and Biology, vol. 49, pp. 2463-2475, 2004.

Yong Long, et al., "3D Forward and Back-Projection for X-Ray CT Using Separable Footprints", IEEE Transactions on Medical Imaging, vol. 29, No. 11, pp. 1839-1850, Nov. 2010.

International Search Report issued Oct. 30, 2012 in Application No. PCT/JP2012/073111(With English Translation).

\* cited by examiner

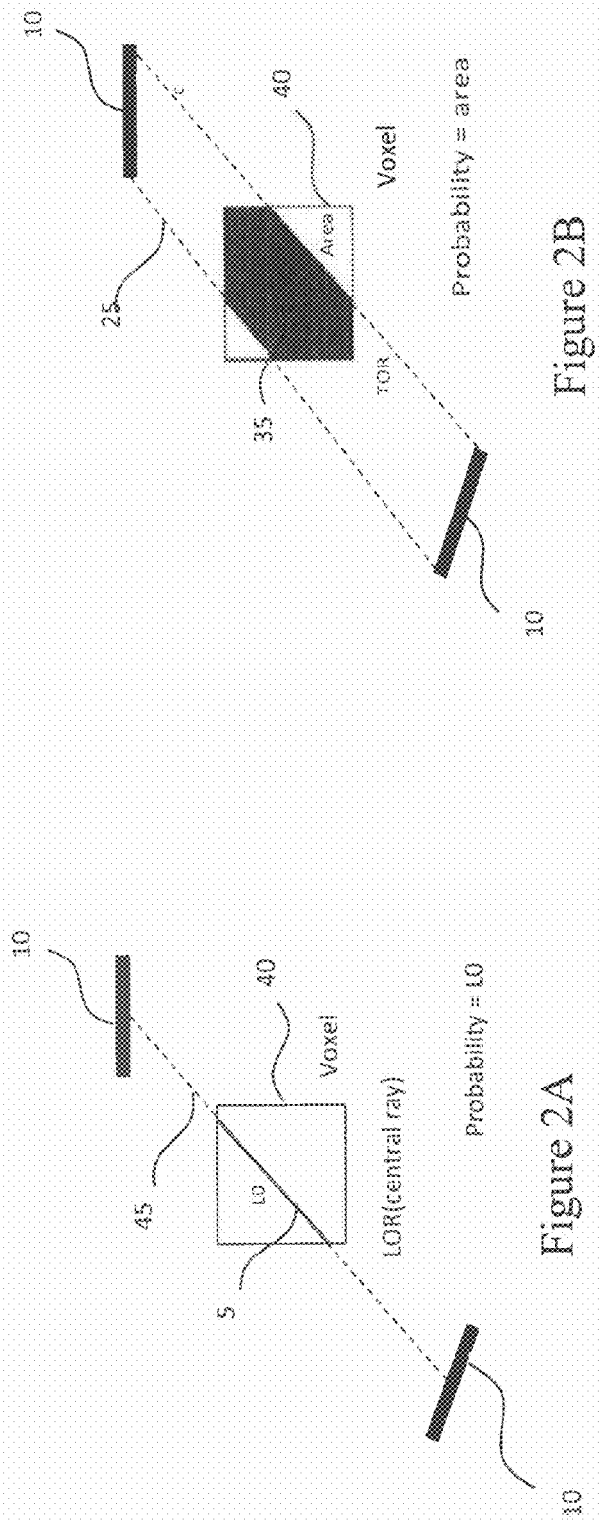
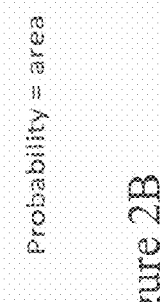
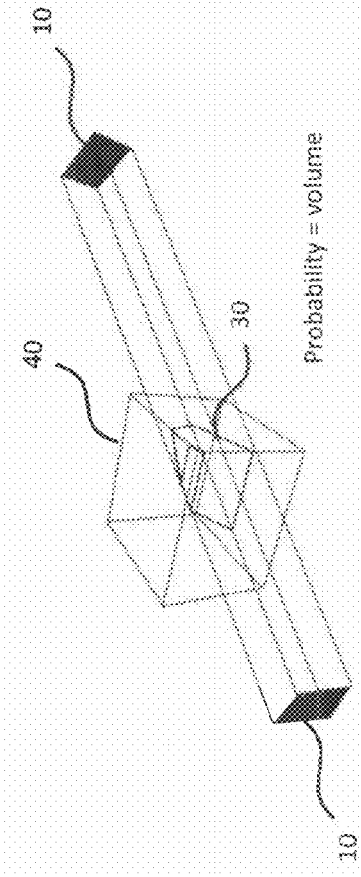
Figure 2B
Figure 2C
Figure 2A

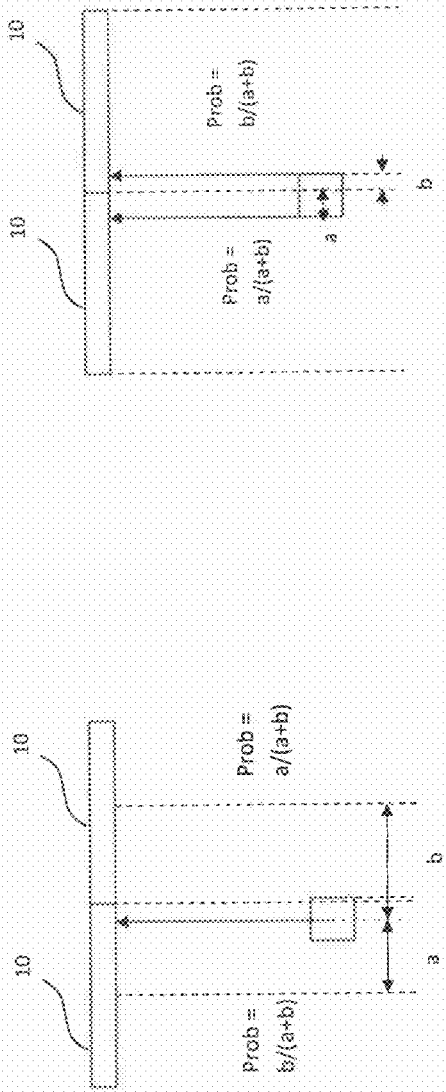
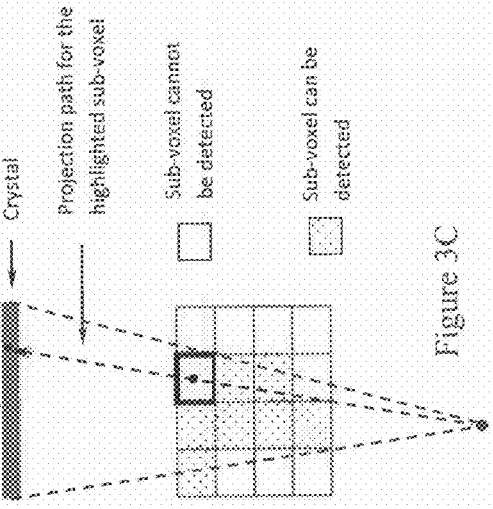
Figure 3A
Figure 3B
Figure 3C

METHOD, DEVICE, AND SYSTEM FOR CALCULATING A GEOMETRIC SYSTEM MODEL USING AN AREA-SIMULATING-VOLUME ALGORITHM IN THREE DIMENSIONAL RECONSTRUCTION

BACKGROUND

1. Field

Embodiments described herein relate to forward and backward projection using area-simulating-volume system model in three-dimensional reconstruction in a medical imaging apparatus.

2. Background

The use of positron emission tomography (PET) is growing in the field of medical imaging. In PET imaging, a radiopharmaceutical agent is introduced into an object to be imaged 15, shown in FIG. 1, via injection, inhalation, or ingestion. After administration of the radiopharmaceutical, the physical and bio-molecular properties of the agent will cause the agent to concentrate at specific locations in the human body (i.e., object 15). The actual spatial distribution of the agent, the intensity of the region of accumulation of the agent, and the kinetics of the process from administration to eventually elimination are all factors that may have clinical significance. During this process, a positron emitter attached to the radiopharmaceutical agent will emit positrons according to the physical properties of the isotope, such as half-life, branching ratio, etc.

The radionuclide emits positrons, and when an emitted positron collides with an electron, an annihilation event occurs, wherein the positron and electron are destroyed. Most of the time, an annihilation event produces two gamma photons at 511 keV traveling at substantially 180 degrees apart which are detected by a pair of crystals. By drawing a line between centers of a pair of crystals 10, i.e., the line-of-response (LOR), or drawing a polyhedron formed by connecting corresponding corners of a pair of crystals 10, i.e., tube-of-response (TOR), one can retrieve the likely location of the original disintegration. While this process will only identify a line (or tube) of possible interaction, by accumulating a large number of those lines (or tubes), and through a tomographic reconstruction process, the original distribution can be estimated. In addition to the location of the two scintillation events, if accurate timing (within few hundred picoseconds) is available, a time-of-flight (TOF) calculation can add more information regarding the likely position of the event along the line (or tube).

The above-described detection process must be repeated for a large number of annihilation events. While each imaging case must be analyzed to determine how many counts (i.e., paired events) are required to support the imaging task, current practice dictates that a typical 100-cm long, FDG (fluorodeoxyglucose) study will need to accumulate several hundred million counts. The time required to accumulate this number of counts is determined by the injected dose of the agent and the sensitivity and counting capacity of the scanner.

Briefly, the PET reconstruction process finds the amount and the location of isotopes (unknown) in the patient from the data recorded in the PET system (known). One of the basic questions in the PET reconstruction process is to find detection probability, which represents the probability of a photon emitted from a voxel that can be detected by a given pair of crystals 10.

To address this question, a certain algorithm is designed to calculate detection probabilities $a_{ij}$ for a line-of-response (LOR) i or tube-of-response (TOR) i and a specific voxel j. A conventional formula used in iterative Ordered Subset Expectation Maximization (OSEM) reconstruction is shown in Equation 1:

$$\overline{f}_j^{k+1} = \frac{\overline{f}_j^k}{Q_j} \sum_{i \in Sub_t} \frac{a_{ij} Y_i}{\sum_{j'=1}^{m} a_{ij'} \overline{f}_{j'}^k + R_i + S_i} \quad (1)$$

In Equation 1, $a_{ij}$ is the probability of voxel j contributing to the $TOR_i$, $Q_j$ is a normalization term by summing all possible $a_{ij}$ over the $Sub_t$, $f_j$ is the activity of voxel j, $Y_i$ represents the detected photons in $TOR_i$, $Sub_t$ is the $t^{th}$ subset, and $R_i$ and $S_i$ are random and scatter counts along $TOR_i$, respectively.

In Equation 1, $a_{ij}$ can generally be divided into many components according to different physical effects, as shown in Equation 2:

$$a_{ij} = c_{ij} \times sensitivity_{ij} \times resolution_{ij} \times attenuation_i \times TOF_{ij} \times \ldots \quad (2)$$

where $c_{ij}$ is the geometric probability, which is an important factor of $a_{ij}$, and is calculated according to the embodiments disclosed herein.

For most of the analytical calculations of $c_{ij}$, an implicit assumption is that radionuclei are distributed homogenously inside the voxel. Therefore, the probability $c_{ij}$ is proportional to the intersected volume between the TOR and the voxel. If the volume of a voxel is a unit, $c_{ij}$ can be directly represented by the intersected volume, as shown in Equation 3:

$$c_{ij} = \frac{\text{intersected volume between tube } i \text{ and voxel } j}{\text{total volume of voxel } j} \quad (3)$$

In practice, the intersected volume is not always easy to calculate, especially for non-parallel-geometry systems such as cone-beam X-ray Computed Tomography (CT), cone-, fan- or parallel-beam Single Photon Emission Computed Tomography (SPECT), and PET.

Quantitative PET reconstruction requires a system response matrix as accurate as possible. Thus, a basic requirement is to accurately calculate the geometric probabilities. In the clinic, the speed of reconstruction is also very important. Therefore, a fast and accurate algorithm is needed to meet this requirement.

BRIEF DESCRIPTION OF THE DRAWINGS

The disclosure will be better understood from reading the description which follows and from examining the accompanying figures. These figures are provided solely as non-limiting examples of the embodiments. In the drawings:

FIGS. 2A-2C illustrate different methods of calculating geometric probabilities;

FIGS. 3A-3C illustrate two-dimensional (2D) methods for calculating an intersected area of a voxel;

DETAILED DESCRIPTION

Figure 1:
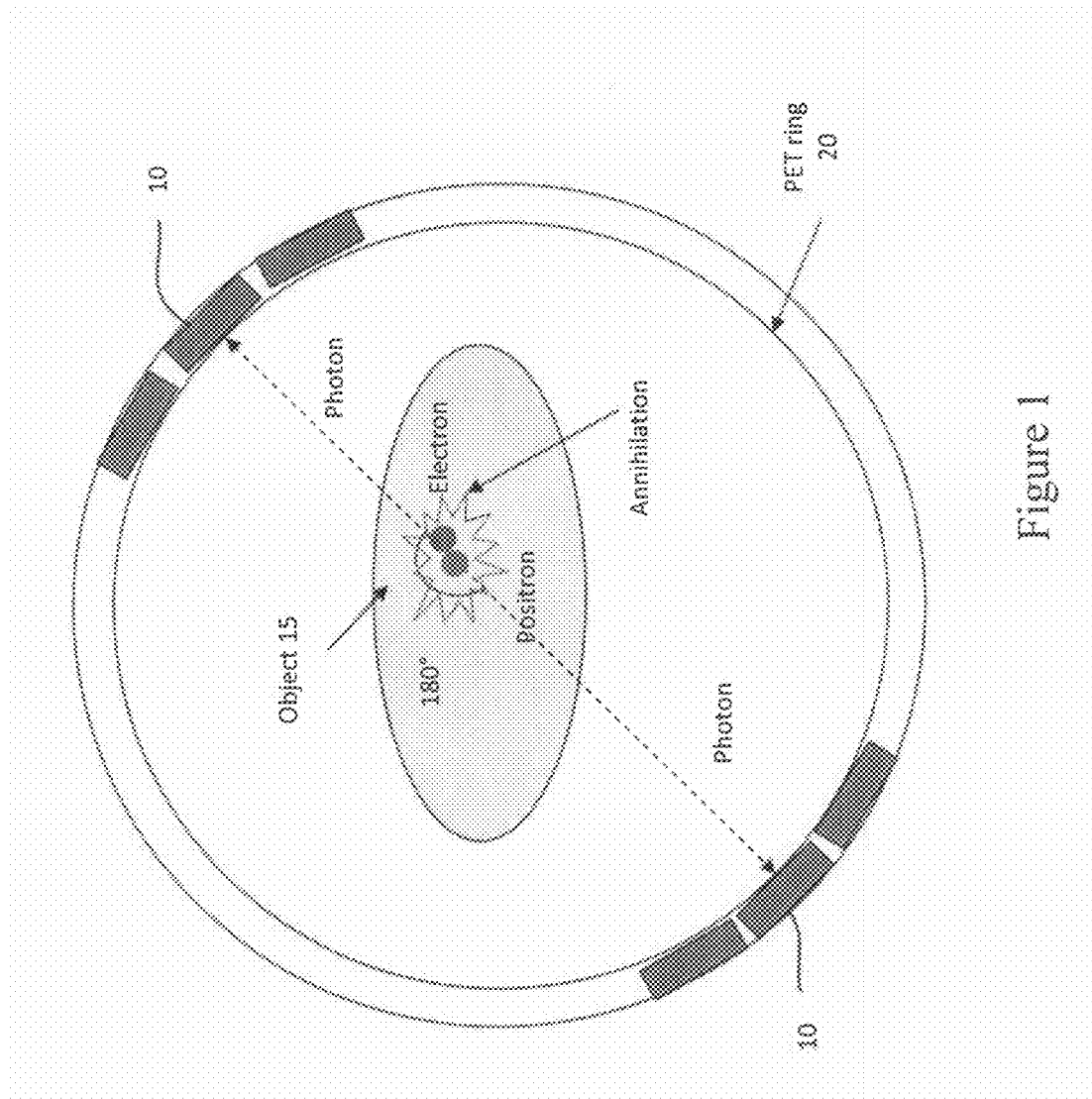
FIG. 1 shows a Positron Emission Tomography (PET) detector ring.

The present disclosure describes a method, device, and system for calculating distance ratios used to calculate a geometric probability between a voxel and a tube-of-response (TOR) defined by two crystals within a reconstruction space of a medical imaging apparatus. The method includes determining a first edge line connecting respective left endpoints of the two crystals in an X-Y plane of the medical imaging apparatus, the first edge line including a first middle point located midway between the left endpoints, determining a second edge line connecting respective right endpoints of the two crystals in the X-Y plane, the second edge line including a second middle point located midway between the right endpoints, determining a middle line of the TOR in the X-Y plane as a line intersecting the first middle point and the second middle point, projecting, in the X-Y plane, a first center point of a first surface of the voxel to the middle line along a direction of the first edge line to define a first projected point, projecting, in the X-Y plane, a second center point of a second surface of the voxel to the middle line along a direction of the second edge line to define a second projected point, calculating a first distance between one of the first and second middle points and the first projected point, and a second distance between the one of the first and second middle points and the second projected point, and determining a first distance ratio in the X-Y plane based on the first distance and the second distance.

The method of the present disclosure further includes determining a center on each of the two crystals defining a line of response. The method also includes determining the first center point of the first surface of the voxel and the second center point of the second surface of the voxel based on an angle between the line of response and a positive X-axis in the X-Y plane.

In addition, the method includes determining a third edge line connecting respective front endpoints of the two crystals in a Y-Z or X-Z plane of the medical imaging apparatus, the third edge line including a first z-line point, determining a fourth edge line connecting respective rear endpoints of the two crystals in the Y-Z or X-Z plane, the fourth edge line including a second z-line point, determining a z-line of the TOR parallel to a Z-axis in the Y-Z or X-Z plane as a line intersecting the first z-line point and the second z-line point, projecting, in the Y-Z or X-Z plane, a third center point of a third surface of the voxel to the z-line along a direction of the third edge line to define a third projected point, projecting, in the Y-Z or X-Z plane, a fourth center point of a fourth surface of the voxel to the z-line along a direction of the fourth edge line to define a fourth projected point, calculating a third distance between one of the first and second z-line points and the third projected point, and a fourth distance between the one of the first and second z-line points and the fourth projected point, and determining a second distance ratio in the Y-Z or X-Z plane based on the third distance and the fourth distance.

Furthermore, the method of the present disclosure also includes calculating an intersected volume by multiplying the first distance ratio by the second distance ratio. The method also describes that the first surface of the voxel and the second surface of the voxel are on opposite sides of the voxel, and that the third surface of the voxel and the fourth surface of the voxel are on opposite sides of the voxel.

As mentioned above, the intersected volume 30 (illustrated in FIGS. 2A-2C) is not easy to calculate. Therefore, many approximate methods are used to overcome the implementation difficulties or to perform calculations in practical amount of time. The aforementioned methods can be classified in three categories, as shown in FIGS. 2A-2C. One-dimensional (1D) methods calculate intersected line length 5 or linear interpolations such as a line-length model (one-ray or multi-ray) or a point-lattice model. FIG. 2A shows an example of one-ray line-length model.

FIG. 2B shows an example of two-dimensional (2D) methods that calculate accurate or approximate intersected area 35 of voxel 40. The methods include a triangle subtraction method, a strip-area model, Gaussian interpolation, rotation interpolation (illustrated in FIG. 3A), a distance-driven method (illustrated in FIG. 3B), and an area-weighted convolutional interpolation. One 2D method used in CT is the so-called distance-driven method, which projects edges of a detector bin and a voxel 40 onto a predetermined plane, and calculates the overlapping areas, as shown in FIG. 3B. This method provides good image quality as compared to a 3D method.

As compared to the other two methods, the three-dimensional (3D) methods provide the best image quality and quantitative accuracy. FIG. 2C shows an example of 3D methods that calculate accurate or approximate intersected volume 30 of voxel 40. The methods include an analytical algorithm that finds all intersected points and calculates the volume, and a subdivision algorithm that subdivides the voxel into a number of sub-voxels and counts the number of sub-voxel centers that are projected inside the crystal 10, as shown in FIG. 3C. In order to calculate the error of the subdivision approach, Equation 4 may be used, $$\text{Error} \leq (2N^2-4)/N^3 \qquad (4)$$

For example, if N is equal to thirty-two (32), then the error is less than or equal to 6.2 percent.

However, the aforementioned methods have certain disadvantages. For example, the 1D and 2D methods are fast, but lose quantitative accuracy and often introduce artifacts, especially in current 3D PET reconstruction. Further, the 3D methods need a relatively long time to calculate geometric probabilities, which encumbers their applications in commercial products. The subdivision method is a typical slow-speed 3D algorithm. For example, to generate geometric probabilities for all possible LORs of a 20-ring PET system and 128*128*20 voxels, it takes about one-hundred-thirty-four (134) hours using $32^3$ sub-voxels even if eight (8) Central Processing Units (CPUs) are used. Furthermore, the distance-driven method is used in CT applications and is not yet extended, or used, in PET applications. Additionally, the direct use of the distance-driven method causes artifacts and asymmetric problems in PET.

An embodiment of the present disclosure calculates the overlapping area between the TOR 25 and voxel 40, and applies this area as the approximate intersected volume 30 in the system response matrix in 3D PET reconstruction. The algorithm of an embodiment of the present disclosure is called the area-simulating-volume (ASV) algorithm, in which the area is calculated as the product of two distance ratios in the X-Y plane and the Y-Z (or X-Z) plane, respectively.

In a cylindrical PET system, the TOR 25 is formed by six (6) planes (i.e., two detector surfaces and four planes formed by connecting eight corners of a pair of crystals 10). Any two crystal surfaces are not parallel to each other in most cases and, consequently, the other four planes are often not parallel to their opposite planes, except in some special cases. This geometric particularity requires specific methods in calculating distance ratios, which differentiates the embodiments of the present disclosure from the methods discussed above that are used in CT.

Choosing the Common Plane

One step of the ASV algorithm is to choose, or select, a proper common plane for calculations of distance ratios. In the distance-driven method used in CT, a fixed Y-Z or X-Z plane is chosen as the common plane that is used to map the edges of the voxel 40 and the edges of the crystal 10. This selection causes some artifacts in PET reconstruction. The issue can be explained by the example illustrated in FIG. 4A. As the given voxel 40 moves closer to the Y-Z plane (i.e., the X-axis in this 2D example), the distance ratio becomes smaller. Thus, this ratio is dependent on the location of the common plane. Thus, different TORs have different algorithm errors depending on the relative positions of the TORs to the Y-Z plane. In this case, visible artifacts are observed in a forward/back projection due to non-uniform errors. For example, suppose TOR 1 and 2 have 5% and 2% calculation errors, respectively. Thus, TOR 1 and TOR 2 can get 100 photons without errors, and get 105 and 102 photons with the above errors, respectively. As a result, those errors produce non-uniformity artifacts. If the algorithm errors are uniform (for example, 3%), then two TORs get the same number of photons without artifacts.

In an embodiment of the present disclosure, an adaptive common plane is selected to overcome the aforementioned issue. This plane passes through two middle points 55 on edge lines of two crystals 10, and is perpendicular to the X-Y plane. For example, in FIG. 4B the common plane is along the middle line 50 (i.e., is perpendicular to the page along middle line 50). The adaptive common planes are different for different TORs, but can always be located at the center of the TOR 25. Note that the ASV method can be applied to TORs having polyhedron shapes. As a result, this method can provide uniform algorithm errors that remove the non-uniformity artifacts discussed above.

Choosing the Edges of a Voxel

The ASV algorithm is an approximate method and may also induce errors due to the algorithm itself. Therefore, there is a need to minimize algorithm errors and make the geometric probabilities close to their real values. Choosing, or selecting, the proper edges of a voxel 40 in the mapping process is an important step in minimizing algorithm errors.

In the ASV algorithm, the edges of a voxel are selected based on the center of a surface. In particular, each voxel 40 has six (6) surfaces, and therefore has six (6) surface centers (indicated by L, R, U, D, F, B in FIG. 5A). Four (4) of the six (6) centers are projected to the common plane to form an intersected area. In an embodiment of the present disclosure, the projection process is separated into two steps.

In the first step, two centers 56 of the voxel 40 are projected to the middle line 50 of the common plane (see FIG. 4B) in the X-Y plane, thereby forming projected points 65. Arrows 52 and 53 are used to show the aforementioned projection from the voxel 40. Arrow 52 is parallel to the left-side edge line of TOR 25, and arrow 53 is parallel to the right-side edge line of TOR 25.

In the second step, the other two centers 56 of the voxel 40 are projected to a line parallel to the Z-axis in the Y-Z or the X-Z plane.

Figures 6A, 6B:
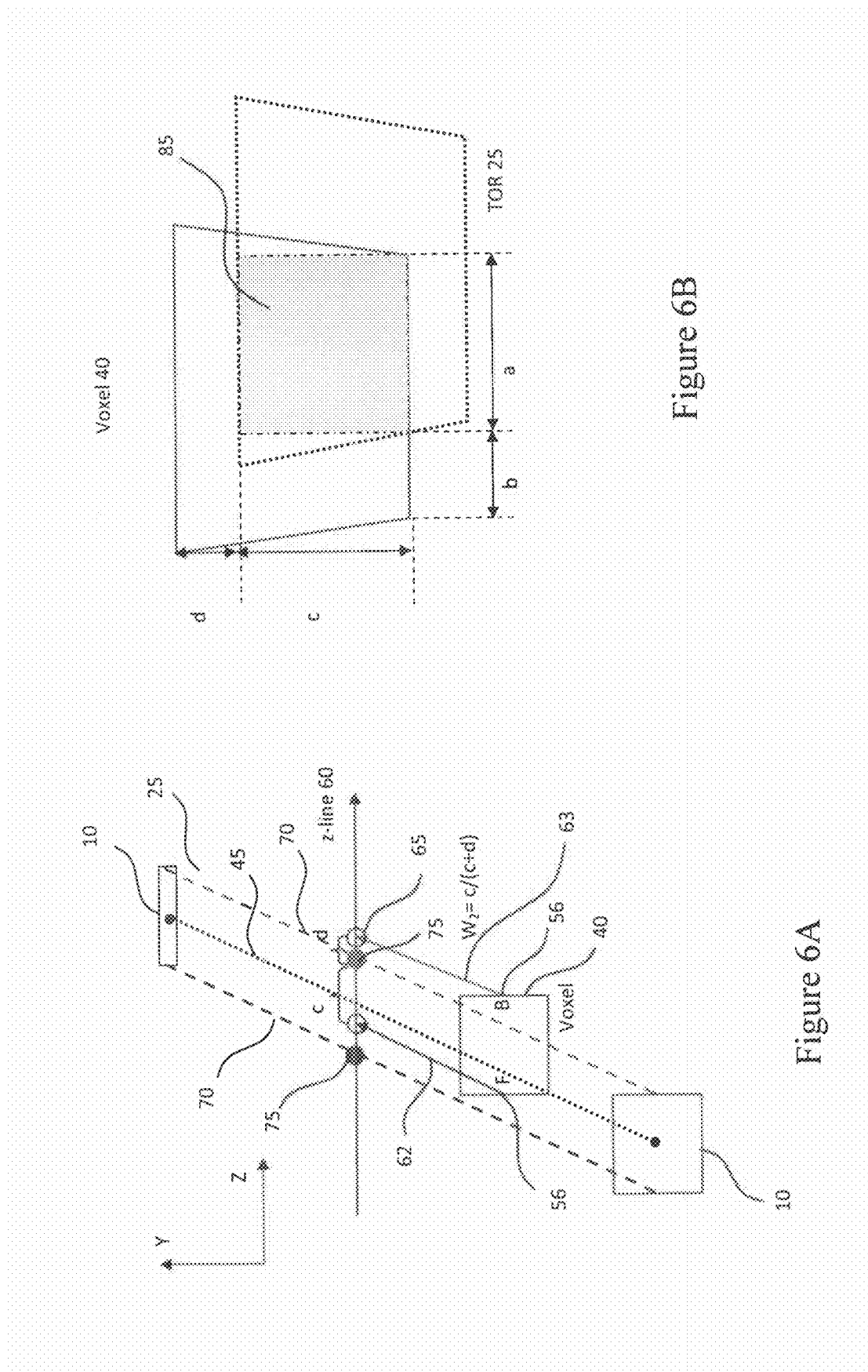
FIGS. 6A and 6B illustrate embodiments for calculating the distance ratio and geometric probability.

As illustrated in FIG. 6A, arrows 62 and 63 are used to show the aforementioned projection from the voxel 40. Arrow 62 is parallel to the left-side edge line 70 of TOR 25, and arrow 63 is parallel to the right-side edge line 70 of TOR 25. More details are provided below in the "Calculating the distance ratio and geometric probability" section.

Figure 5C:
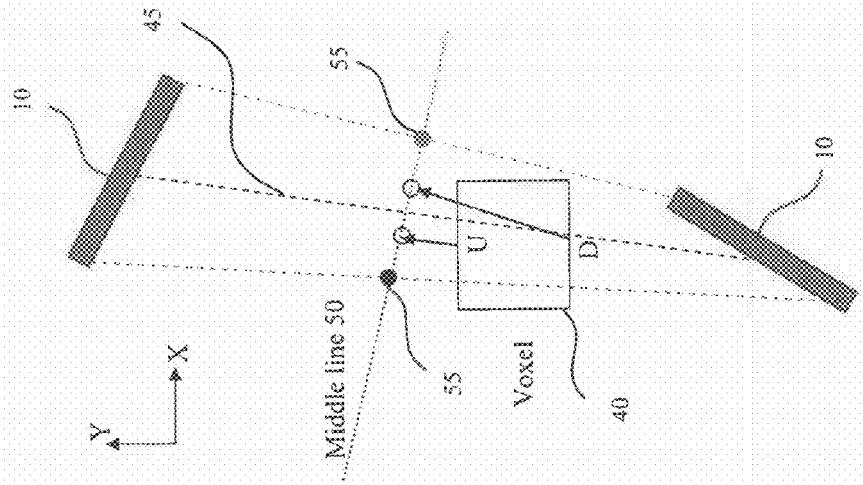
FIGS. 5A-5C illustrate embodiments for selecting the proper edges of a voxel for projection.
Figure 5A:
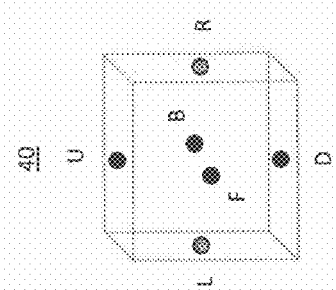
Figure 5B:
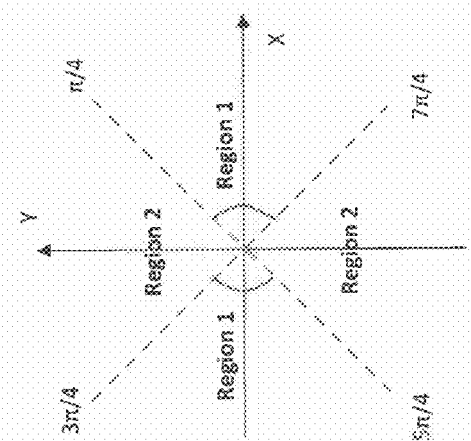

In the first step, two centers 56 are chosen, or selected, from L-R or U-D depending on the direction of the TOR 25. The angle between the central line 45 (connecting centers of two crystals 10) and the +X-axis dictates which of the centers (L-R or U-D) to select. FIG. 5B shows different regions in which the aforementioned angle may be located. For example, when the angle between the central line 45 (connecting centers of two crystals 10) and the +X-axis is located in Region 1, centers U and D are selected, otherwise, centers L and R are selected. The following example can reveal the reasons behind this selection. FIG. 5C shows an example of erroneously selecting U and D. Accordingly, if U and D are selected instead of L and R in FIG. 5C, the distance ratio between the middle points 55 and the center points 56 equals one (1). However, the intersected volume 30 is not equal to one (1).

In the second step, centers F and B are always chosen, or selected, to be projected. However, the selection of the Y-Z or the X-Z plane depends on the angle between the central line 45 and the +Z-axis. If the angle is located in Region 1, the X-Z plane is selected, otherwise the Y-Z plane is selected.

Calculating the Distance Ratio and Geometric Probability

Figure 7A:
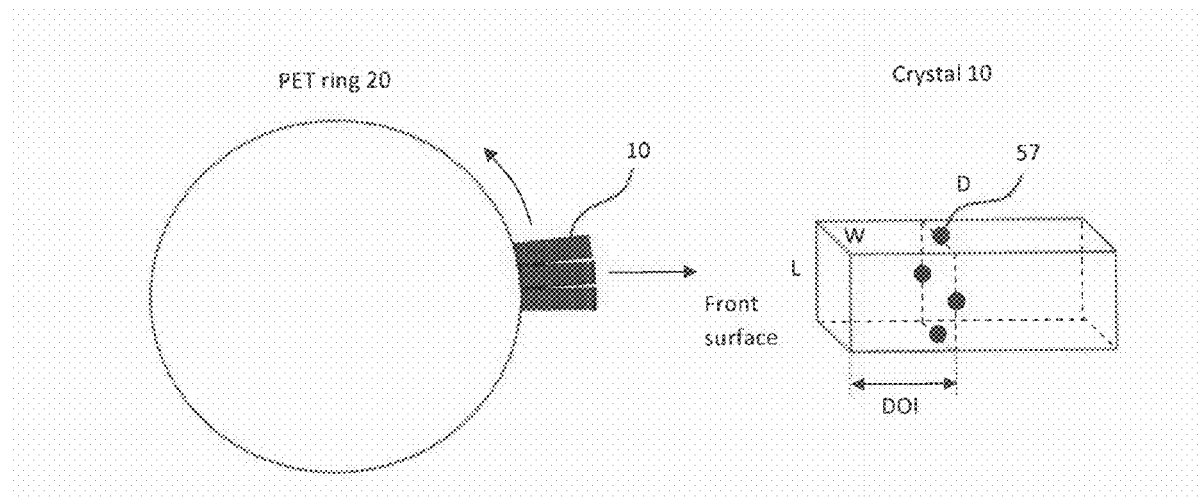
FIGS. 7A and 7B illustrate a selection of edges of crystals and a projection direction of the centers of a voxel.
Figure 7B:
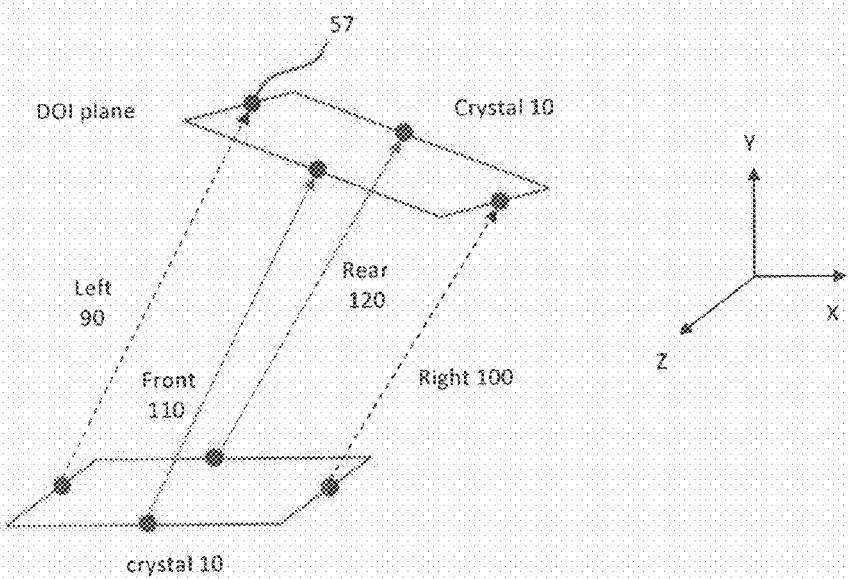

After the edges (i.e., centers on surfaces) of the voxel 40 are determined, the ASV algorithm projects those centers 56 to the middle line 50 or z-line 60 (discussed below) along certain directions, thereby forming projected points 65. To determine the projection directions, four middle points 57 are selected from the sides of a rectangle (shown in FIG. 7A) on the average depth-of-interaction (DOI) plane of each crystal, which is determined by the average depth of interaction between photons and crystals, e.g., 40% of the crystal 10 length. Then, the projection direction is given as follows: the left 90 and right 100 lines determine the projection directions of L (or U) and R (or D) on the voxel 40 in the X-Y plane, and the front 110 and rear 120 lines determine the projection directions of F and B on the voxel 40 in the Y-Z/X-Z plane, as shown in FIG. 7B.

As discussed above, center L-R or U-D is projected to the middle line 50, and center F-B is projected to the line parallel to the Z-axis (named a "z-line" 60), as shown in FIG. 6A. The reason for selecting the z-line 60 for projecting F-B, is that two crystals 10 of a TOR 25 form two rectangles (or a segment) after being projected to the Y-Z or the X-Z plane. In this case, the central line 45 connecting central points of two crystals 10 is parallel to the other two lines 70 connecting middle points of the side surfaces of crystals 10, at the left side or the right side, as is shown in FIG. 6A. Therefore, the distance ratio is independent of the z-line 60 location and non-uniformity artifacts are not produced. Note that points 75 on z-line 60 may correspond to points 55 on the middle line 50, or may be different from the points 55 on the middle line 50.

It is noted that when the voxel 40 is located between the edge lines of the TOR 25, the ratio distance is equal to one (1).

Figure 4B:
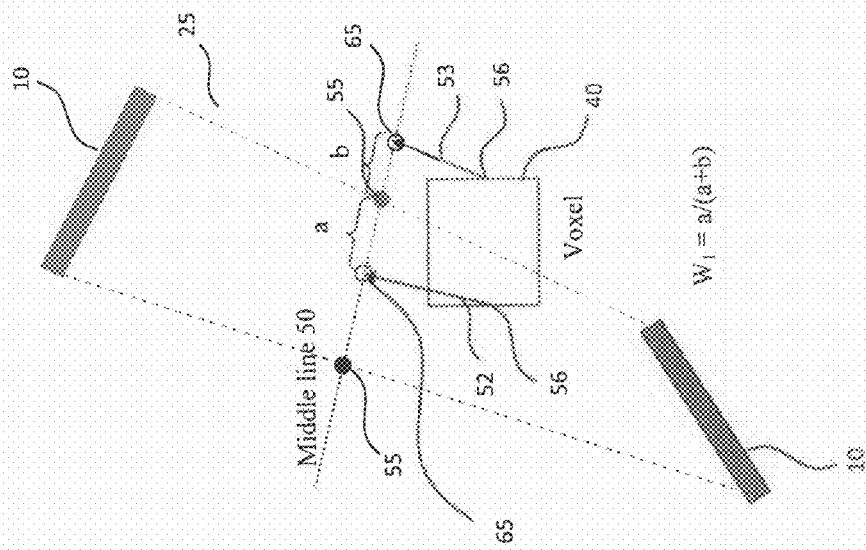
FIGS. 4A and 4B show embodiments for selecting a plane for calculations of distance ratios.
Figure 4A:
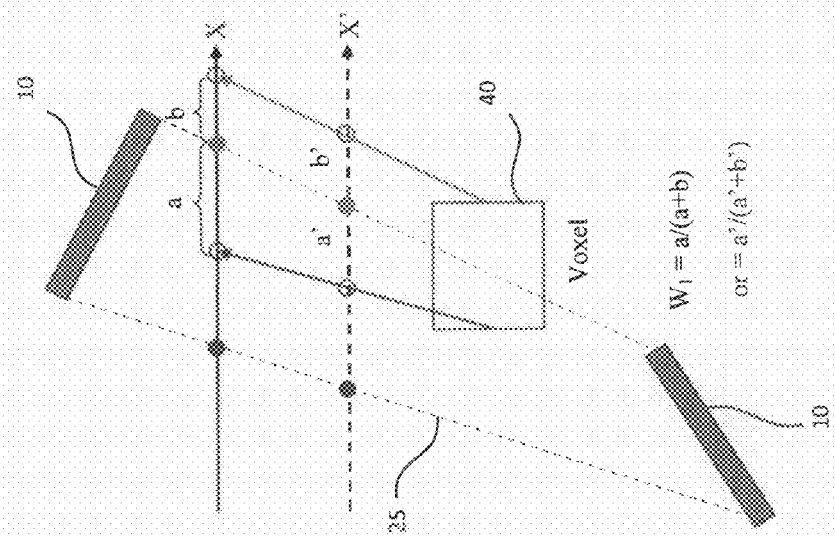

In the ASV algorithm, the geometric probability is equal to the product of distance ratios $W_1$ and $W_2$, which is calculated in the X-Y plane and the Y-Z (or X-Z) plane, as illustrated in FIG. 4B and FIG. 6A. In other words, in Equation 5 below:

$$c_{ij} = (W_1)_{ij} \times (W_2)_{ij} = \left(\frac{a}{a+b} \times \frac{c}{c+d}\right)_{ij} \quad (5)$$

FIG. 6B illustrates the projection of a voxel 40 to the common plane, and an intersected shape between the TOR 25 and the common plane. Thus, a×c is an intersected area 85 between voxel 40 and TOR 25 in the common plane. In one embodiment the height of this intersected part is assumed to be a unit, which is not always true. Then, $c_{ij}$ becomes an intersected volume 30. This concept is the reason that the algorithm of the present disclosure is referred to as "area-simulating-volume."

In summary, an embodiment of the present disclosure calculates an overlapping area between a TOR and a voxel, and applies the calculated overlapping area as the approximate intersected volume in a system response matrix in 3D PET reconstruction. The ASV algorithm calculates the area as the product of two distance ratios in the X-Y and the Y-Z (or X-Z) plane, respectively. One example of calculating the distance ratio in the X-Y plane includes 1) finding the middle line of a TOR, the middle line being the line connecting the middle points of two edge lines of TOR; 2) projecting two center points of edges of a voxel to the middle line along the direction of two edge lines; and 3) finding the distance ratio between the two (2) middle points and the two (2) projected points.

Figure 8A:
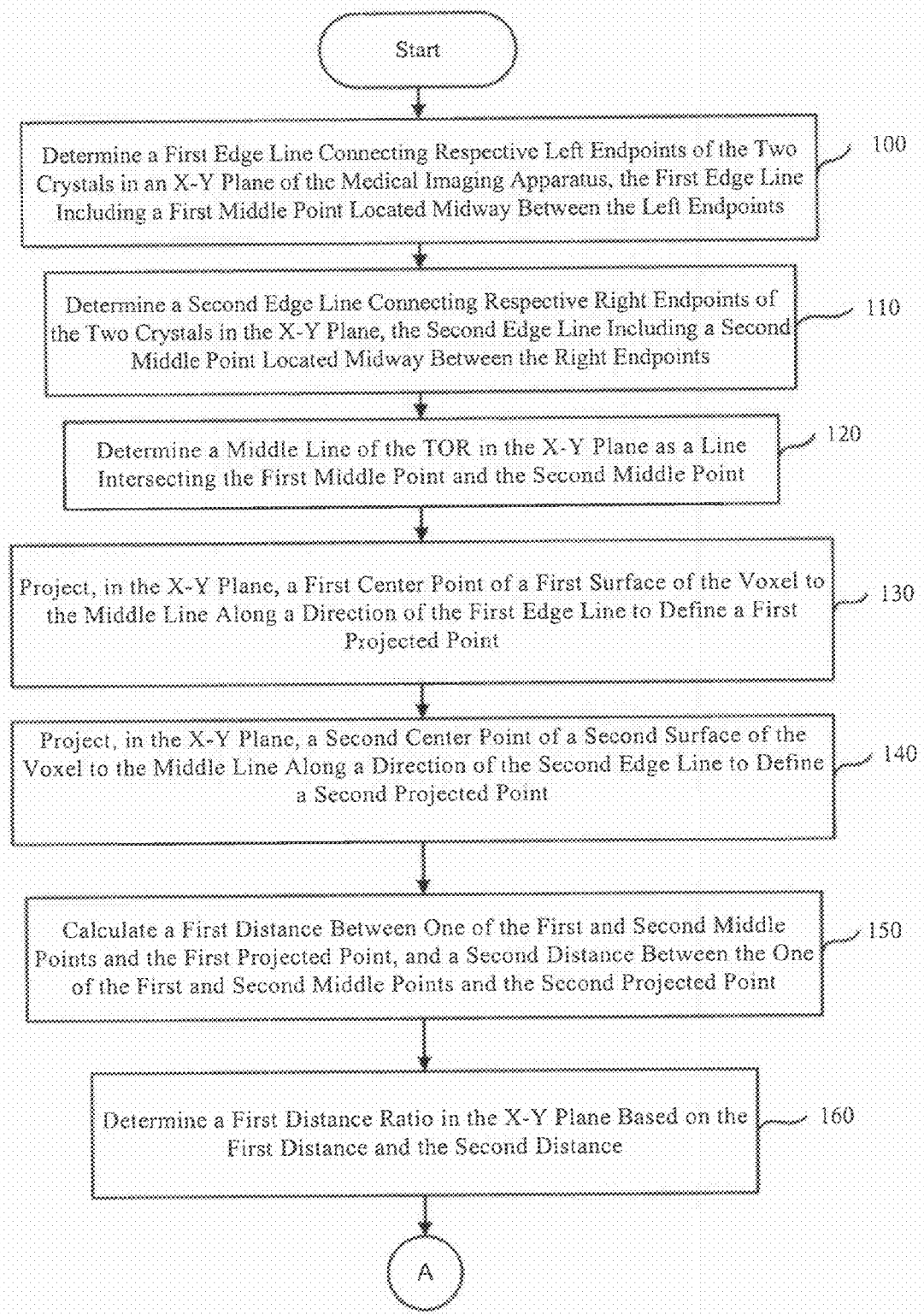
FIGS. 8A and 8B illustrate a flow chart of a method of the present disclosure.
Figure 8B:
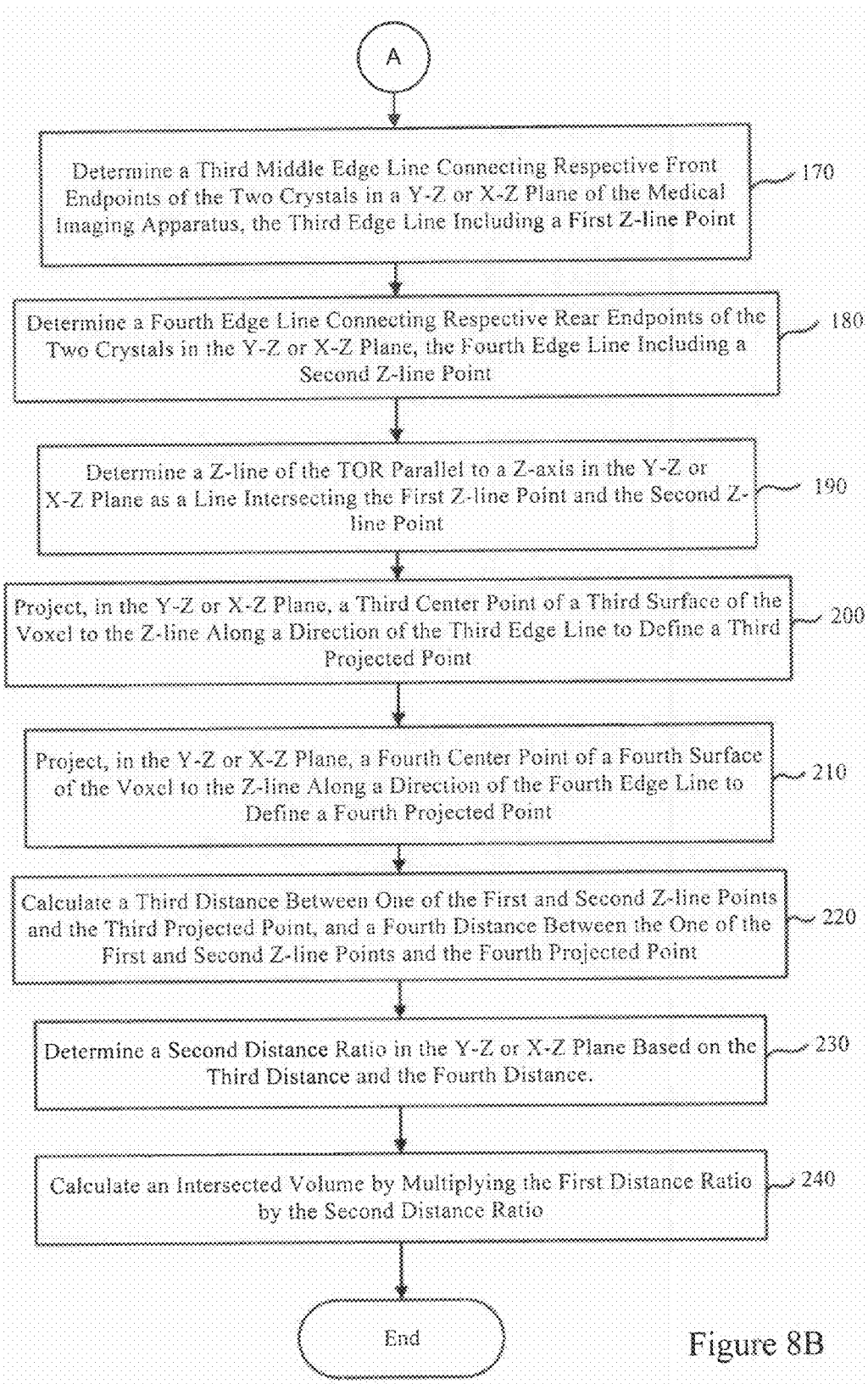

FIGS. 8A and 8B illustrate a method for calculating distance ratios used to calculate a geometric probability between a voxel 40 and a TOR 25 defined by two crystals 10 within a reconstruction space of a medical imaging apparatus such as PET. In step 100, a first edge line connecting respective left endpoints of the two crystals in an X-Y plane of the medical imaging apparatus is determined, the first edge line including a first middle point located midway between the left endpoints. In step 110, a second edge line connecting respective right endpoints of the two crystals in the X-Y plane is determined, the second edge line including a second middle point located midway between the right endpoints.

Next, in step 120, a middle line of the TOR in the X-Y plane is determined, the middle line being a line intersecting the first middle point and the second middle point. In step 130, a first center point of a first surface of the voxel is projected, in the X-Y plane, to the middle line along a direction of the first edge line to define a first projected point. Then, in step 140, a second center point of a second surface of the voxel is projected, in the X-Y plane, to the middle line along a direction of the second edge line to define a second projected point.

In step 150, a first distance between one of the first and second middle points and the first projected point is calculated, and a second distance between the one of the first and second middle points and the second projected point is also calculated. Next, in step 160, a first distance ratio in the X-Y plane based on the first distance and the second distance is determined.

Furthermore, in step 170, a third edge line connecting respective front endpoints of the two crystals in a Y-Z or X-Z plane of the medical imaging apparatus is determined, the third edge line including a first z-line point. In step 180, a fourth edge line connecting respective rear endpoints of the two crystals in the Y-Z or X-Z plane is determined, the fourth edge line including a second z-line point.

Next, in step 190, a z-line of the TOR parallel to a Z-axis in the Y-Z or X-Z plane is determined, the z-line being a line intersecting the first z-line point and the second z-line point. In step 200, a third center point of a third surface of the voxel is projected, in the Y-Z or X-Z plane, to the z-line along a direction of the third edge line to define a third projected point. Then, in step 210, a fourth center point of a fourth surface of the voxel is projected, in the Y-Z or X-Z plane, to the z-line along a direction of the fourth edge line to define a fourth projected point.

In step 220, a third distance between one of the first and second z-line points and the third projected point is calculated, and a fourth distance between one of the first and second z-line points and the fourth projected point is also calculated. Next, in step 230, a second distance ratio in the Y-Z or X-Z plane is determined based on the third distance and the fourth distance. Finally, in step 240, an intersected volume is calculated by multiplying the first and second distance ratios.

Figure 9B:
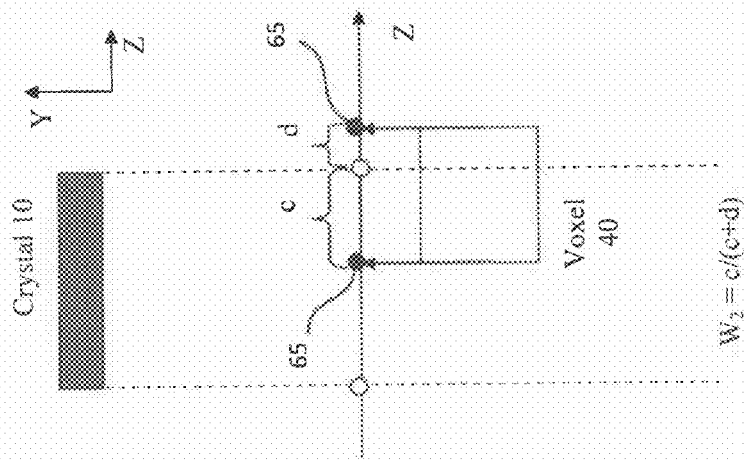
FIGS. 9A and 9B illustrate an application of a method of the present disclosure in a parallel-beam SPECT imaging apparatus.
Figure 9A:
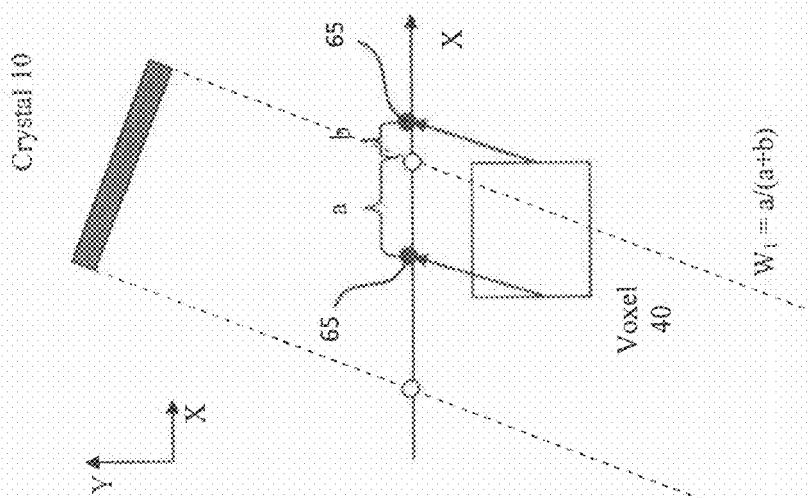

The methods of the present disclosure may also be applied to other medical imaging modalities such as CT and SPECT. In CT imaging, the ASV algorithm may be used to calculate the geometric probabilities $c_{ij}$ even if the TOR shape degrades from a polyhedron to a cone, which will in fact simplify the algorithm. In SPECT imaging, the TOR shape can vary from a cuboid, triple prism to pyramid for a parallel-beam collimator, fan-beam collimator, or cone-beam collimator. The ASV algorithm may be used with little modification since the polyhedron TOR can include all the aforementioned shapes. For example, in SPECT with a parallel-beam collimator, two distance ratios can be calculated similar to those in PET, but the common plane is now fixed at Y=0 or X=0, and the projection direction is the same for a pair of edges of a voxel since the lines connecting crystal edges are parallel to each other. FIGS. 9A and 9B show the application of the ASV algorithm in a SPECT imaging apparatus with a parallel-beam collimator. Specifically, FIG. 9A shows a distance ratio in the X-Y plane, and FIG. 9B shows a distance ratio in the Y-Z plane.

Image Quality and Calculation Speed

The area-simulating-volume algorithm produces good image quality, which is relatively close to the image quality generated by a 3D method (e.g., the subdivision method). However, the ASV algorithm takes much less time than the intersected-volume method. For example, the ASV algorithm takes about 247 seconds to generate all geometric probabilities for 80 angles of a 48-ring PET, but the intersected-volume method needs 29626 seconds (100 times difference, using 4 CPUs).

Figure 10:
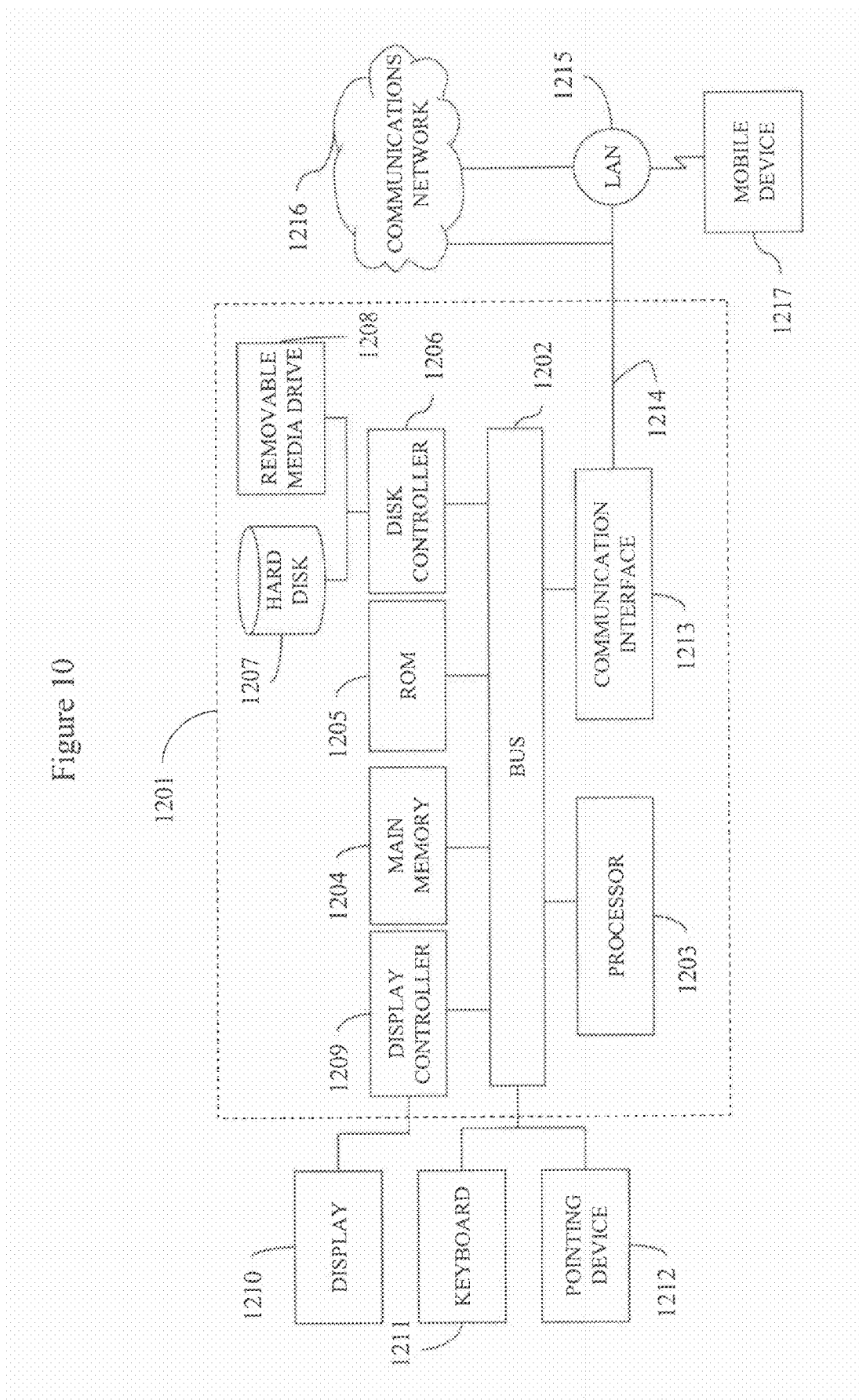
FIG. 10 illustrates a computer system upon which an embodiment of the present disclosure may be implemented.

Various components of the PET system described above can be implemented using a computer system or programmable logic. FIG. 10 illustrates a computer system 1201 upon which embodiments of the present disclosure may be implemented. The computer system 1201 may include, for example, the different processing units (i.e., a determining unit, a projecting unit, a calculating unit, a distance ratio determining unit, and an intersected volume calculating unit) of a reconstruction device and/or a PET system, which perform the above-described process.

The computer system 1201 includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as the touch panel display 101 or a liquid crystal display (LCD), for displaying information to a computer user. The computer system includes input devices, such as a keyboard 1211 and a pointing device 1212, for interacting with a computer user and providing information to the processor 1203. The pointing device 1212, for example, may be a mouse, a trackball, a finger for a touch screen sensor, or a pointing stick for communicating direction information and command selections to the processor 1203 and for controlling cursor movement on the display 1210.

The computer system 1201 performs a portion or all of the processing steps of the present disclosure in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1201, for driving a device or devices for implementing the invention, and for enabling the computer system 1201 to interact with a human user. Such software may include, but is not limited to, device drivers, operating systems, and applications software. Such computer readable media further includes the computer program product of the present disclosure for performing all or a portion (if processing is distributed) of the processing performed in implementing the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1203 for execution. A computer readable medium may take many forms, including but not limited to, non-volatile media or volatile media. Non-volatile media includes, for example, optical, magnetic disks, and magneto-optical disks, such as the hard disk 1207 or the removable media drive 1208. Volatile media includes dynamic memory, such as the main memory 1204. Transmission media, on the contrary, includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1201 may receive the data on the telephone line and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an integrated services digital network (ISDN) card. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc.). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method for calculating distance ratios used to calculate a geometric probability between a voxel and a tube-of-response (TOR) defined by two crystals within a reconstruction space of a medical imaging apparatus, the method comprising:
    determining a first edge line connecting respective left endpoints of the two crystals in an X-Y plane of the medical imaging apparatus, the first edge line including a first middle point located midway between the left endpoints;
    determining a second edge line connecting respective right endpoints of the two crystals in the X-Y plane, the second edge line including a second middle point located midway between the right endpoints;
    determining a middle line of the TOR in the X-Y plane as a line intersecting the first middle point and the second middle point;
    projecting, in the X-Y plane, a first center point of a first surface of the voxel to the middle line along a direction of the first edge line to define a first projected point;
    projecting, in the X-Y plane, a second center point of a second surface of the voxel to the middle line along a direction of the second edge line to define a second projected point;
    calculating a first distance between one of the first and second middle points and the first projected point, and a second distance between the one of the first and second middle points and the second projected point; and
    determining a first distance ratio in the X-Y plane based on the first distance and the second distance.

2. The method of claim 1, further comprising:
    determining a center on each of the two crystals defining a line of response.

3. The method of claim 2, further comprising:
    determining the first center point of the first surface of the voxel and the second center point of the second surface of the voxel based on an angle between the line of response and a positive X-axis in the X-Y plane.

4. The method of claim 1, further comprising:
    determining a third edge line connecting respective front endpoints of the two crystals in a Y-Z or X-Z plane of the medical imaging apparatus, the third edge line including a first z-line point;
    determining a fourth edge line connecting respective rear endpoints of the two crystals in the Y-Z or X-Z plane, the fourth edge line including a second z-line point;
    determining a z-line of the TOR parallel to a Z-axis in the Y-Z or X-Z plane as a line intersecting the first z-line point and the second z-line point;
    projecting, in the Y-Z or X-Z plane, a third center point of a third surface of the voxel to the z-line along a direction of the third edge line to define a third projected point;
    projecting, in the Y-Z or X-Z plane, a fourth center point of a fourth surface of the voxel to the z-line along a direction of the fourth edge line to define a fourth projected point;
    calculating a third distance between one of the first and second z-line points and the third projected point, and a fourth distance between the one of the first and second z-line points and the fourth projected point; and
    determining a second distance ratio in the Y-Z or X-Z plane based on the third distance and the fourth distance.

5. The method of claim 4, further comprising:
    calculating an intersected volume by multiplying the first distance ratio by the second distance ratio.

6. The method of claim 4, wherein
    the third surface of the voxel and the fourth surface of the voxel are on opposite sides of the voxel.

7. The method of claim 1, wherein
    the first surface of the voxel and the second surface of the voxel are on opposite sides of the voxel.

8. A reconstruction device for calculating distance ratios used to calculate a geometric probability between a voxel and a tube-of-response (TOR) defined by two crystals within a reconstruction space of a medical imaging apparatus, the reconstruction device comprising:
    a determining unit configured to
        determine a first edge line connecting respective left endpoints of the two crystals in an X-Y plane of the medical imaging apparatus, the first edge line including a first middle point located midway between the left endpoints,
        determine a second edge line connecting respective right endpoints of the two crystals in the X-Y plane, the second edge line including a second middle point located midway between the right endpoints, and
        determine a middle line of the TOR in the X-Y plane as a line intersecting the first middle point and the second middle point;
    a projecting unit configured to project, in the X-Y plane, a first center point of a first surface of the voxel to the middle line along a direction of the first edge line to define a first projected point, and to project, in the X-Y plane, a second center point of a second surface of the voxel to the middle line along a direction of the second edge line to define a second projected point;
    a calculating unit configured to calculate a first distance between one of the first and second middle points and the first projected point, and a second distance between the one of the first and second middle points and the second projected point; and
    a distance ratio determining unit configured to determine a first distance ratio in the X-Y plane based on the first distance and the second distance.

9. The reconstruction device of claim 8, wherein
    the determining unit is further configured to determine a center on each of the two crystals defining a line of response.

10. The reconstruction device of claim 9, wherein
the determining unit is configured to determine the first center point of the first surface of the voxel and the second center point of the second surface of the voxel based on an angle between the line of response and a positive X-axis in the X-Y plane.

11. The reconstruction device of claim 8, wherein
the determining unit is further configured to
determine a third edge line connecting respective front endpoints of the two crystals in a Y-Z or X-Z plane of the medical imaging apparatus, the third edge line including a first z-line point,
determine a fourth edge line connecting respective rear endpoints of the two crystals in the Y-Z or X-Z plane, the fourth edge line including a second z-line point, and
determine a z-line of the TOR parallel to a Z-axis in the Y-Z or X-Z plane as a line intersecting the first z-line point and the second z-line point;
the projecting unit is further configured to project, in the Y-Z or X-Z plane, a third center point of a third surface of the voxel to the z-line along a direction of the third edge line to define a third projected point, and to project, in the Y-Z or X-Z plane, a fourth center point of a fourth surface of the voxel to the z-line along a direction of the fourth edge line to define a fourth projected point;
the calculating unit is further configured to calculate a third distance between one of the first and second z-line points and the third projected point, and a fourth distance between the one of the first and second z-line points and the fourth projected point; and
the distance ratio determining unit is further configured to determine a second distance ratio in the Y-Z or X-Z plane based on the third distance and the fourth distance.

12. The reconstruction device of claim 11, further comprising:
an intersected volume calculating unit configured to calculate an intersected volume by multiplying the first distance ratio by the second distance ratio.

13. The reconstruction device of claim 11, wherein
the third surface of the voxel and the fourth surface of the voxel are on opposite sides of the voxel.

14. The reconstruction device of claim 8, wherein
the first surface of the voxel and the second surface of the voxel are on opposite sides of the voxel.

15. A Positron Emission Tomography (PET) system for calculating distance ratios used to calculate a geometric probability between a voxel and a tube-of-response (TOR) defined by two crystals within a reconstruction space of the PET system, the PET system comprising:
a determining unit configured to
determine a first edge line connecting respective left endpoints of the two crystals in an X-Y plane of the PET system, the first edge line including a first middle point located midway between the left endpoints,
determine a second edge line connecting respective right endpoints of the two crystals in the X-Y plane, the second edge line including a second middle point located midway between the right endpoints, and
determine a middle line of the TOR in the X-Y plane as a line intersecting the first middle point and the second middle point;
a projecting unit configured to project, in the X-Y plane, a first center point of a first surface of the voxel to the middle line along a direction of the first edge line to define a first projected point, and to project, in the X-Y plane, a second center point of a second surface of the voxel to the middle line along a direction of the second edge line to define a second projected point;
a calculating unit configured to calculate a first distance between one of the first and second middle points and the first projected point, and a second distance between the one of the first and second middle points and the second projected point; and
a distance ratio determining unit configured to determine a first distance ratio in the X-Y plane based on the first distance and the second distance.

* * * * *